United States Patent [19]

Fok et al.

[11] Patent Number: 5,451,413
[45] Date of Patent: Sep. 19, 1995

[54] YEAST DERIVATIVE AND METHOD TO IMPROVE BREAD QUALITY

[75] Inventors: Jacob J. Fok, Delft; Jan D. R. Hille, Wouw; Berend Van Der Veen, Delft, all of Netherlands

[73] Assignee: Gist-Brocades, B.V., Netherlands

[21] Appl. No.: 122,326

[22] Filed: Sep. 16, 1993

[30] Foreign Application Priority Data

Sep. 17, 1992 [EP] European Pat. Off. ........... 92202852

[51] Int. Cl.$^6$ .................. A21D 2/00; A21D 8/04; A23L 1/28; A23B 7/154
[52] U.S. Cl. .................. 426/19; 426/60; 426/62
[58] Field of Search ............... 426/19, 60, 62

[56] References Cited

U.S. PATENT DOCUMENTS

| 2,368,384 | 1/1945 | Selman et al. ........... 426/60 X |
| 2,875,064 | 2/1959 | Glabe . |
| 4,341,871 | 7/1982 | Langejan . |
| 5,290,959 | 3/1994 | Rice .................. 426/312 X |

FOREIGN PATENT DOCUMENTS

| 0040237 | 5/1981 | European Pat. Off. . |
| 0262669 | 4/1988 | European Pat. Off. . |
| 0487122 | 5/1992 | European Pat. Off. . |
| PCT/NL800-0038 | 5/1981 | Netherlands . |

OTHER PUBLICATIONS

Copy of European Search Report (3 pages).
Copy of Isolation . . . Concentrate Article (4 pages).
Cereal Chem. vol. 61(5), pp. 428–431—Isolation of a Fermentation Stimulant from Yeast—Protein Concentrate—Davis, et al, Oct. 1984.

*Primary Examiner*—Jeanette Hunter
*Assistant Examiner*—Choon P. Koh
*Attorney, Agent, or Firm*—Bierman and Muserlian

[57] ABSTRACT

The present invention relates to a method for improving the rheological properties of dough and quality of baked products by addition of a yeast derivative, preferably in combination with a reducing agent and/or enzyme preparations having amylase, hemicellulase, oxido reductase and/or protease activities.

8 Claims, No Drawings

YEAST DERIVATIVE AND METHOD TO IMPROVE BREAD QUALITY

The present invention relates to a bread improver composition which comprises a yeast derivative and to a method for improving the rheological properties of dough and quality of baked products by addition of a yeast derivative, preferably in combination with a reducing agent and/or enzyme preparations having amylase, hemicellulase, oxido-reductase and/or protease activities.

It is well known that the quality of a baked product, defined in terms of the product's volume, its internal structure, softness (bread), crispiness (biscuits), and the various organoleptic parameters depends on the rheological properties of the dough, in particular dough elasticity and extensibility. These properties are dependent on the quality of the wheat flour used, more specifically on the quality of the gluten proteins. The gluten network developed from these proteins during mixing and proofing determines the elasticity/extensibility of the dough. The gluten network is also strongly involved in the ability of the dough to retain gas.

The use of strong flour has several disadvantages, the dough is less extensible, smooths more slowly and has resistance during mixing and excessive elasticity during moulding, which causes tearing of dough pieces during shaping, hindered rise during the final proof, limited and irregular development of products in the oven and low loaf volumes. Technological solutions for these problems include decreased dough temperature, reduced proofing time, addition of reducing agents like L-cysteine or fungal or bacterial proteases.

These reducing agents may be part of bread improvers. Other constituents of bread improvers will also help to improve bread quality, e.g. emulsifiers condition the dough and improve dough gas retaining capacity.

In a conventional kneading system for breadmaking dough development is such that the gas retaining capacity of the dough is rather limited directly after mixing. In these cases a dough resting period is built in. This resting period can be shortened drastically through mechanical dough development by the use of high-speed mixers, or by using chemically activated dough development. In the latter case L-cysteine is used in combination with ascorbic acid. Besides reduction of total process time mixing time is reduced and dough quality is improved because of better machineability and extensive relaxation of the dough.

In the production of biscuits, esp. semi-sweets and crackers, sodium metabisulfite is added to obtain optimal relaxation of the dough. A chemical alternative like L-cysteine is only effective in this type of dough in very large quantities. As an alternative for these chemical compounds proteases can be used. However, using this type of enzyme tolerance is greatly reduced in this system.

EP-A-0262669 describes fat compositions suitable for use in bakeries or confectioners. These compositions contain in addition to the fat component, disrupted yeast cells. The methods of disrupting yeast cells, disclosed in this document, all result in yeast cell suspensions of which the enzyme activities are inactivated.

In the present invention it was found surprisingly that a yeast derivative, preferably in combination with a reducing agent and enzyme preparations having preferably amylase, hemicellulase, oxidoreductase activities gave unexpected results on dough elasticity/extensibility, gas retaining capacity and bread quality and that combination of the yeast derivative and a neutral protease lead to an excellent and constant dough extensibility in biscuits preparation.

The present invention therefore provides a yeast derivative comprising from 90 to 100% dry matter, from 40 to 65% (N×6.25) protein based on dry matter content and from 2 to 150 micromole SH per g yeast derivative, and having a catalase activity from 2 to 250 U/g and a gassing power of from 0 to 100 ml $CO_2$ per hour and per g at 30° C.

The protein content of the yeast derivative of the present invention is calculated in terms of the nitrogen content as determined by the Kjeldahl method and multiplied by a factor 6.25 to obtain an estimate of the amount of proteins, peptides and free amino acids present in the yeast derivative. A minor part of this crude protein consists of L-cysteine (an SH-group containing amino acid) and glutathione. Glutathione is a tripeptide one of which is L-cysteine. The total amount of SH-containing molecules in the yeast derivative is usually in between 2 and 150 micromoles of SH per gram of material.

The yeast derivative of the present invention is used to improve the rheological properties of dough and the quality of baked products. The yeast derivative may be added to the dough alone or together with a reducing agent (e.g. L-cysteine), and amylase, hemicellulase, oxidoreductase and/or protease.

A preferred oxido reductase is glucose oxidase. Examples of other preferred enzymes are sulphydryl oxidase, lipoxygenase, and peroxidase.

The dough generally comprises flour, water, yeast and salt. It may also contain oxidants, shortening, emulsifiers and further enzymes. Examples of oxidants are potassium bromate, ascorbic acid, or salts of this acid. These types of oxidants are generally dosed in a range of 10 to 200 ppm on weight calculated on the amount of flour.

Commonly used emulsifiers are soya lecithin, diacetyltartaric acid esters of mono/diglycerides, sodium or calcium stearoyllactylate, and fatty acid esters of mono- and polyglycerol. Added quantities usually range from 0.1 to 0.5% by weight relative to the amount of flour used.

Examples of commonly used enzymes in dough preparation are fungal and bacterial α-amylases, amyloglucosidase, cellulase, hemicellulase (pentosanase) and protease. Added quantities strongly depend on the purity of the preparations used.

The present invention therefore also provides an improver composition which comprises the yeast derivative and at least one of L-cysteine, an amylase, a hemicellulase, an oxidoreductase and a protease. Composition and dosage of the bread improver should be advantageously chosen so, that in the prepared dough is present in between 0.01 and 5.0% by weight of yeast derivative, preferably between 0.05 and 1.0%, and more preferably in between 0.1 and 0.9% in between 5 and 70 ppm L-cysteine, and preferably in between 10 and 50 ppm, fungal and bacterial α-amylase in between 10 and 400 PU per kg of flour, and preferably in between 25 and 250 PU/kg flour, hemicellulase in between 1 and 10000 HU/kg flour, preferably 5 to 5000 HU/kg flour, glucose oxidase in between 1 and 300 Sarrett units/kg flour, preferably 5 to 150 Sarrett units/kg flour, and protease in between 1000 and 150000 PC/kg flour, preferably between 3000 and 50000 PC units per kg flour.

α-Amylase activity was determined using Phadebas ™ tablets from Pharmacia. In this method the solubilization of dye labelled starch by α-amylase in a buffer pH=5.5 during 15 minutes at 30° C. is measured spectrophotometrically. α-Amylase activity is expressed in Phadebas Units (PU) using an *Aspergillus oryzae* fungal α-amylase preparation of 10,000 PU/g as an internal standard. One Phadebas Unit defined in this way equals about 10 SKB units, used in the baking industry.

Fungal hemicellulase activity was determined by measuring the amount of reducing sugars produced over a predetermined time period in the micro-assay as described by Leathers T. D., Kurtzman, C. P., Detroy, R. W. (1984) Biotechnol. Bioeng. Symp., 14, 225. In this paper the hemicellulase unit (HU) is also defined.

One Sarrett unit of glucose oxidase activity is defined as the amount of enzyme, which catalyses the $O_2$ uptake of 10 $mm^3$/minute in a Warburg manometer using a 3.3% glucose solution in phosphate buffer pH 5.9 at 30° C. in the presence of excess $O_2$ and catalase activity.

One PC unit is defined as the amount of enzyme necessary to catalyse the hydrolysis of a caseine substrate during 30 minutes in a TRIS buffer of pH 7.0 and at 37° C. in the presence of calcium and magnesium, such that, after stopping the reaction with trichloro acetic acid, the hydrolysate has an absorbance at 275 nm equal to a tyrosine solution of 1.5 μg/ml.

The yeast derivative may be produced in a variety of ways. Preferably the yeast is of the Saccharomyces genus, such as *Saccharomyces cerevisiae*.

Two main routes of preparation are:
drying of the yeast cream and grinding
heat treatment of the cream and drying.

In the first route the yeast cream can be filtered, extruded and dried in a fluidized-bed and afterwards ground into a powder.

In the second route the yeast cream can be heat-treated for example at 45°–55° C. for 1 to 8 hours, preferably 1.5 to 4 hours. Afterwards the cream is dried either on a belt-dryer, or by spray-drying.

Preferably the second route, which is heat-treatment of the cream followed by drying, is chosen.

The yeast derivative of the present invention has a dry matter content in between 90 and 100%, a protein content in between 40 and 65% (N×6.25), and more preferably in between 50 and 60% (N×6.25), an SH-content in between 2 and 150 micromole per g, and more preferably in between 10 and 100 micromole per g (determined according to the method described by Ellman, G. L. (Arch. Biochem. Biophys. 82 (1959), 70) and enzyme activities which are normally found in baker's yeast, such as catalase activity in between 2 and 250 U/g. The yeast derivative may also include other enzyme activities like hexokinase, alcoholdehydrogenase, NADH-oxidase, cytochrome c peroxidase or a proteinase. Gassing power of the yeast derivative is in between 0 and 100 ml $CO_2$ per hour and per gram at 30° C. Preferably the gassing power is less than 50 ml $CO_2$ per hour per gram at 30° C. More preferably the gassing power is between 10 and 40 ml $CO_2$ per hour and per gram at 30° C. The yeast derivative is advantageously produced in a powder form.

One Unit of catalase activity is defined as the amount of enzyme which decomposes one micromole of hydrogen peroxide per minute at 25° C. and pH 7.5.

The yeast derivative or improver composition may be added to dough, for example bread dough or biscuit dough, before baking. The yeast derivative is preferably added to the dough in a range of 0.01 to 5.0% by weight relative to the amount of flour and more preferably in a range of 0.05 to 1%. Combined with other additives in an improver composition and dosage of improver should be in symphony with the above mentioned ranges.

The present invention will be further demonstrated by the following examples. It should be noted that the present invention is by no means limited to these examples.

EXAMPLE I (reference example)

The yeast derivative was produced by pouring out 250 mL of yeast cream (21.8% DM) of *Saccharomyces cerevisiae* (baker'yeast) in a stainless steel pan (diameter 20 cm). This pan was placed on a hot plate (diameter 35 cm) of which the temperature was adjusted to 200° C. After reaching 100° C. the yeast cream was kept for 5 seconds at this temperature. Afterwards the pan was cooled in a waterbath at 20° C. to room temperature and the material lyophilized. To get homogeneous powder form product the obtained material was ground by using a small-scale electric coffee grinder.

The obtained product had a dry matter content of 97.3%, a protein content of 58.6% (N×6.25), an SH-content of 33 micromole/g, a catalase activity of 45 U/g of powder and no residual gassing power.

Extension of the heat treatment of the yeast cream in the pan at 100° C. to 50 seconds lead to a product having a dry matter content of 97.1%, a protein content of 58.3% (N×6.25), an SH-content of 18 micromole/g, and no residual enzyme activity.

EXAMPLE II

The yeast derivative was produced by grinding 40 g Fermipan ® (Gist-brocades) instant yeast for 30 seconds in a small-scale coffee grinder. The obtained product did not produce $CO_2$, had an SH-content of 31 micromole/g, and showed enzyme activity, amongst others of 198 U/g catalase activity.

EXAMPLE III

Preparation of puploaves in a short breadmaking process was done by mixing 200 g of wheat flour, 1.2 g Fermipan ® instant yeast, 4 g salt, 3 g sugar, 50 ppm ascorbic acid (AA) and 111 mL water in a pinmixer for 6 minutes and 15 seconds. The dough temperature is 27° C. Machineability of the dough is analyzed by hand by a qualified baker. Directly after mixing the dough is divided into two 150 g dough pieces and proofed for 25 minutes in a proofing cabinet at 31° C. and 85% RH.

After this period the doughs are again analyzed by hand to check machineability, moulded, shaped and panned and given a final proof of 70 minutes in a proofing cabinet at 31° C. and 85% RH. Afterwards the fully proofed doughs are baked in an electric oven at 250° C. for 20 minutes. After cooling down to room temperature the volumes of the loaves are obtained by the rapeseed displacement method. Afterwards break and shred of the breads is analysed. After 24 hrs of storage the crumb quality is analysed by a qualified baker. Results are given in Table I.

From these results it is clear, that doughs prepared from this relative strong wheat flour were too stiff and too elastic during moulding, leading to a hindered rise in the final proof and to poorly developed breads after baking. Addition of L-cysteine as a reducing agent lead to too much breakdown of the elasticity of the dough resulting in only a small increase in loaf volume. Addition of the enzyme inactive yeast derivative as a reducing agent normalized dough elasticity leading to a further increase of loaf volume and better bread quality. Addition of 0.3% of the enzyme active yeast derivative gave excellent results.

TABLE I

| | Machineability during moulding | Break* & Shred | Crumb* struct. | Loaf vol. (ml) |
|---|---|---|---|---|
| Reference (50 ppm AA) | too stiff | 5 | 5 | 450 |
| +25 ppm L-cysteine | too slack | 5 | 5 | 470 |
| +0.6% yeast derivative (enzyme inactive) | normal | 6 | 6 | 490 |
| +0.3% yeast derivative (enzyme active) | normal | 6 | 6 | 495 |
| +0.3% yeast derivative (enzyme active) +25 ppm L-cysteine | excellent | 8 | 8 | 525 |
| +0.3% yeast derivative (enzyme inactive) +25 ppm L-cysteine | too slack | 5 | 6 | 465 |

*Figures are given on a scale in between 1 (bad) and 10 (excellent).

Surprisingly, however, the combination of the yeast derivative and L-cysteine at the same dosages as being used as single ingredients, gave an excellent dough elasticity throughout the whole breadmaking process leading to optimal machineability and optimal loaf volumes. Combination of L-cysteine and small amounts of enzyme inactive yeast derivative (0.3%) resulted already in a decrease in dough and bread quality compared to the dough and bread quality obtained by enzyme inactive yeast derivative alone.

EXAMPLE IV

Preparation of pup loaves in a short breadmaking process as described in Example II, using the same recipe, however, extended with 20 ppm Fermizyme ® P$_{200}$ (Gist-brocades, 4500 FAU/G), being a fungal α-amylase and 150 ppm Fermizyme ® H$_{400}$ (Gist-brocades, 5000 HU/g), being a hemicellulase, gave the results as shown in Table II.

The combination of fungal α-amylase and fungal hemicellulase enables the production of a good quality of bread showing a regular break and shred (results not shown), a fine crumb structure and a good crumb quality and softness.

However, introducing an extra small amount of the enzyme active yeast derivative increased bread quality: loaf volume and crumb quality are greatly increased. At the same time crumb firmness during a storage period of 72 hours is decreased. Introducing the mutant bacterial α-amylase (R 123 C which is mutant 15 as described in EP 409 299) gave the expected increase in crumb softness during storage. However, combination of a smaller quantity of the mutant bacterial alpha-amylase and a small amount of the enzyme active yeast derivative (0.2%) gave a synergistic effect

TABLE II

| | Machineability before final proof | Crumb quality | Crumb** firmness (%) | Loaf volume (mL) |
|---|---|---|---|---|
| Reference* | normal | 7 | 100 | 560 |
| +0.3% yeast derivative (enzyme active) | excellent | 8 | 90 | 600 |
| +150 ppm bact. amylase | normal | 7 | 75 | 565 |
| +100 ppm bact. amylase +0.2% yeast derivative (enzyme active) | excellent | 8 | 67 | 600 |

* = 50 ppm AA + 20 ppm Fermizyme ® P$_{200}$ + 150 ppm Fermizyme ® H$_{400}$)
** = Crumb firmness was analyzed using a Stevens Texture Analyzer after 72 hrs of storage at room temperature. The value for the reference was set at 100%.
a)Bacterial alpha-amylase is a mutant bacterial α-amylase (Gist-brocades, described in EP 409 299).

on crumb softness during storage, which was larger than the optimal softness increase obtained by the mutant bacterial alpha-amylase.

From these experiments it can be stated that this combination of fungal and bacterial enzymes and the powder form yeast derivative gave an excellent machineability, optimal loaf volume and an improved crumb softness.

EXAMPLE V

In a baking trial producing standard dutch white tin bread in a short breadmaking process 3500 g wheat flour, 2.5% Koningsgist ® (compressed yeast, Gist-brocades), 2% salt, 1.1% sugar, 0.4% enzyme active soya flour, 0.5% crude soyalecithin, 50 ppm ascorbic acid (AA) and 53% water are mixed in a Kemper spiral mixer (350 rotations at speed 1, followed by 1200 rotations at speed 2). The dough temperature is 28° C. Dough machineability is analyzed by hand by a qualified baker. The dough is divided into 6 pieces of 900 g. These pieces are moulded and given a first proof of 35 minutes in a proofing cabinet at 30° C. and 85% RH. After this stage dough machinabiliy is analyzed again by hand by the qualified baker and the dough pieces are moulded, shaped and panned and given a final proof of 70 minutes in a proofing cabinet at 30° C. and 85% RH. Afterwards the doughs are baked in an electric oven at 210° C. for 30 minutes. After cooling down to room temperature loaf volumes are measured by the rapeseed displacement method. Results are shown in Table III. Loaf volumes are an average of volume measurements of 4 loaves of bread.

TABLE III

| | Machineability before final proof | Loaf volume (mL) |
|---|---|---|
| Reference* | too stiff | 3350 |
| +50 ppm Maxazyme ® GOP** | too stiff | 3300 |
| +0.3% yeast derivative (enzyme active) | normal | 3610 |
| +50 ppm Maxazyme ® GOP + 0.3% yeast derivative (enzyme active) | excellent | 3950 |

*recipe described in the text above the Table.
**Maxazyme ® GOP is a fungal glucose oxidase (Gist-brocades) standardised on 1500 Sarrett Units/g.

Ascorbic acid alone in this short process introduced large resistance in the dough during mixing, excessive elasticity during moulding, causing tearing of the dough pieces during shaping, hindered rise during the final proof and limited and irregular development of products in the oven resulting in relatively small loaf volumes. Introducing glucose oxidase at a 50 ppm dosage level does not really change the situation. The dough remains too stiff to show good elasticity resulting in increase in loaf volume.

In the case that instead of glucose oxidase 0.3% enzyme active yeast derivative is introduced the elasticity of the dough after mixing and during proofing increases resulting in normal machineability and in an increase in loaf volume.

However, combination of glucose oxidase and yeast derivative leads to a synergistic action of both ingredients leading to an excellent dough machineability and an additional increase of loaf volume.

EXAMPLE VI

Cream crackers were prepared using an all in straight dough procedure in which 155 g soft wheat flour, 23.5 g hydrogenated vegetable shortening, 4.7 g glucose, 3.1 g skimmed milk powder, 1 g salt and 52.5 g of water were mixed for 10 minutes to a final temperature of 30° C.

Rest times were varied between 5 and 30 minutes. The dough was sheeted according to a fixed reduction scheme to a 1.5 mm sheet using a rondo brake and manually assessed for extensibility and elasticity by an experienced baker. The sheet was docked and cut into 5×5 cm pieces and baked at 280° C. during 7 minutes in a conventional electric oven.

Using a neutral bacterial protease ex *Bacillus subtilis* (Fermizyme ® B500) alone and in combination with enzyme inactive or enzyme active yeast derivative attempts were made to reduce the elasticity of the reference dough.

The results of these trials are shown in table IV.

TABLE IV

| | Extensibility | Biscuit quality |
| --- | --- | --- |
| Reference* +40 ppm protease | too elastic depending on rest time from elastic to too slack. | thick, uneven shaped depending on rest time thick and uneven to thin and burnt |
| +20 ppm protease +0.8% yeast derivative (enzyme inactive) | normal to slightly slack | intermediate, uneven shaped and slightly coloured |

TABLE IV-continued

| | Extensibility | Biscuit quality |
| --- | --- | --- |
| +20 ppm protease +0.4% yeast derivative (enzyme active) | normal and constant | excellent, even shaped and coloured |

From these results it is clear that addition of neutral bacterial protease gave varying results in dough extensibility depending on the length of the rest time. Combination of this neutral bacterial protease with the enzyme inactive yeast derivative in an optimum dosage of 0.8% led to normal and constant extensibility of the dough during all rested resting periods and to an excellent biscuit quality. A 0.4% dosage of enzyme active yeast derivative showed to be the optimum amount in combination with the neutral bacterial protease to get a better result as described for the enzyme inactive yeast derivative.

We claim:

1. A yeast derivative comprising from 90 to 100% dry matter, from 40 to 65% (N×6.25) protein, and from 2 to 150 micromole SH per g of yeast derivative, and having a catalase activity from 2 to 250 U/g and a gassing power of from 0 to 100 ml $CO_2$ per hour and per g at 30° C.

2. A yeast derivative according to claim 1 which comprises from 50% to 60% (N×6.25) protein.

3. A yeast derivative according to claim 1 which comprises from 10 to 100 micromole SH per g yeast derivative.

4. An improver composition comprising a yeast derivative of claim 1 and at least one compound selected from the group consisting of L-cysteine, amylase, hemicellulase, oxidoreductase, protease and reducing agent.

5. A dough comprising an improver composition as claimed in claim 4 and flour, water, yeast and salt.

6. A dough according to claim 5 which further comprises at least one of an oxidant, shortening, an emulsifier and an enzyme.

7. A process for preparing bread which comprises forming a dough as claimed in claim 5 and baking said dough.

8. A process for preparing hard-dough biscuit which comprises mixing flour, water and salt with a yeast derivative of claim 1 and baking said dough.

* * * * *